(12) United States Patent
Waring et al.

(10) Patent No.: US 7,538,090 B1
(45) Date of Patent: May 26, 2009

(54) EXOGENOUS SURFACTANT PROTEIN B MIMIC

(75) Inventors: Alan J. Waring, Irvine, CA (US); Frans J. Walther, Hermosa Beach, CA (US); Larry M. Gordon, Del Mar, CA (US); Joseph A. Zasadzinski, Santa Barbara, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 144 days.

(21) Appl. No.: 11/133,812

(22) Filed: May 19, 2005

Related U.S. Application Data

(60) Provisional application No. 60/573,171, filed on May 21, 2004.

(51) Int. Cl.
*A61K 38/16* (2006.01)
*A61K 35/42* (2006.01)
*C12P 13/16* (2006.01)

(52) U.S. Cl. .................. 514/12; 530/324; 435/112; 424/557

(58) Field of Classification Search ................ None
See application file for complete search history.

(56) References Cited

U.S. PATENT DOCUMENTS 6,180,142 B1   1/2001   Taeusch 6,660,833 B1   12/2003   Walther et al.

OTHER PUBLICATIONS

Hawgood, et al., Biochimica et Biophysica Acta, 1998, 1408, 150-160.*

* cited by examiner

*Primary Examiner*—Andrew D Kosar
*Assistant Examiner*—Satyanarayana R Gudibande
(74) *Attorney, Agent, or Firm*—Blakely Sokoloff Taylor & Zafman LLP

(57) ABSTRACT

A composition including a C terminal region having residues corresponding to a peptide identified by PDB ID: 1RG3; an N terminal region having residues corresponding to a peptide identified by PDB ID: 1RG4; and a disulfide linkage between the residues near the C terminal region and the N terminal region. A composition including an exogenous peptide comprising amino acid residues comprising a C terminal region; amino acid residues comprising an N terminal region; a helix-loop-helix conformation between the residues comprising the C terminal region and the residues including the N terminal region; and at least one disulfide linkage between the residues comprising the C terminal region and the residues including N terminal region, wherein the residues including the C terminal region and the residues comprising the N terminal region have an amphiphatic property, and wherein the peptide has an a biological activity comparable to native surfactant protein SP-B. A method including delivering to a body a composition comprising an exogenous peptide having a biological activity comparable to native surfactant protein SP-B. A kit including an exogenous peptide having a biological activity comparable to native surfactant protein SP-B; and a treatment agent different from the peptide.

8 Claims, 12 Drawing Sheets

MinminB2cys (34 res.)
CWLCRALIKRIQAMIPKGGRMLPQLVCRLVLRCS 34

CWLCRALIKRIQAMIPKGGRMLPQLVCRLVLRCS
rhhhhhhhhhhherrpr4rrlap56hhhhhrlrhx
 12345678910        11111

```
                      ....,....1....,....2....,....3....,....4
            AA        |CWLCRALIKRIQAMIPKGGRMLPQLVCRLVLRCS|
            PROF_sec  | HHHHHHHHHHHHH          HHHHH EEEE |
            Rel_sec   |9037888888884336678822676500033229|
subset:     SUB_sec   |L..HHHHHHHH...LLLLL..HHHH.......L|

3st:        P_3_acc   |eebieebieibeeeieeeeeieebbiebebeie|
            Rel_acc   |0102422285245243956413231213133327|
subset:     SUB_acc   |....e...ei.ee.i.eeee............e|
```

FIG. 4A

Mini-B sequence      CWLCRALIKRIQAMIPKGGRMLPQLVCRLVLRCS
residue conformation rhhhhhhhhhhhhhp56paaarhhhhhhhhhhhr
                     |         |         |         |
residue number       1        10        20        30 h = alpha helix
r = random
a = antiparallel beta sheet
p = parallel beta sheet
56 = type III beta turn

FIG. 4B

Each Picture is 400um x 400um

EXOGENOUS SURFACTANT PROTEIN B MIMIC

CROSS-REFERENCE TO RELATED APPLICATIONS

This application claims the benefit of the earlier filing date of U.S. Provisional Patent Application No. 60/573,171, filed May 21, 2004, and incorporated herein by reference.

STATEMENT REGARDING FEDERALLY SPONSORED RESEARCH OR DEVELOPMENT

This invention was made with Government support under Contract/Grant Nos. 008223-07, RO1 HL 55534, RO1 HL 51177 from the National Institute of Health (NIH), and TRDRP 11 RT-0222 from the Tobacco Related Disease Research Program of the University of California. The United States Government has certain rights in the invention.

FIELD

Surfactants and uses thereof.

DESCRIPTION OF RELATED ART

A surfactant may be described as a surface-active agent that lowers surface tension of water or saline. In biological systems, native surfactant provides maximum absorption that lowers surface tension and improves lung compliance. Surfactant is an essential substance for expansion of the alveoli, or air sacs of the lungs. Naturally occurring surfactants include several surfactant proteins (SP): A, B, C, and D. Proteins B and C are important because they enable the surfactant to adhere to alveolar surfaces. Surfactant Protein B (SP-B) is a critical protein to the activity of lung surfactant. SP-B as a component in surfactant is responsible for adsorption of the surfactant to the air-fluid interface, and therefore is necessary for optimum surfactant function.

A current use of surfactant supplements is in an endotracheal application to relieve respiratory distress. One condition that generally requires a surfactant supplement is neonatal respiratory distress syndrome (RDS). This condition may occur in prematurely born infants whose lungs have not yet completely developed. These infants typically do not have sufficient or properly functioning surfactant in their lungs that is required for normal lung function. Administration of a surfactant supplement may improve oxygenation and lung compliance. However, many surfactant supplements are derived from animal sources such as cow or pig lung lavage. These surfactant supplements have the potential of being contaminated with viral or prion-like components. Also, the use of surfactant supplements from native material tends to be expensive because of the limited amounts of natural surfactant that can be isolated from cow or pig lavage.

Adult (acute) respiratory distress syndrome (ARDS) may be described as the rapid onset of progressive dysfunction of the lungs, usually associated with the dysfunction of other organs due to the inability to take up oxygen. It is a catastrophic clinical syndrome that typically manifests as fulminant acute lung injury with diffuse bilateral pulmonary infiltrates, hypoxemia despite the administration of high concentrations of inspired oxygen, normal left ventricular end-diastolic pressure (as evidenced by a normal pulmonary capillary occlusion pressure), and reduced pulmonary compliance. Patients with acute lung injury typically have a mean alveolar oxygen pressure to fraction of oxygen in inspired air (PaO2/FiO2) ratio of less than 300 torr, while those with ARDS have a ratio less than 200 torr. According to these definitions, the difference between acute lung injury and ARDS is the degree of oxygenation abnormality. The condition is associated with extensive lung inflammation and small blood vessel injury in all affected organs.

Current treatment for ARDS consists of mechanical ventilation along with careful attention to fluid balance and a supportive breathing technique called positive end expiratory pressure (PEEP). These are combined with continuing treatment of the precipitating illness or injury. Most ARDS treatments do not involve surfactant replacement therapy. Even if the ARDS is cured by current treatments, a study found that survivors may have persistent functional disability one year after discharge from the intensive care unit, most commonly reflected in muscle wasting and weakness.

The predominant risk factors for the development of ARDS are sepsis and Systemic Inflammatory Response Syndrome (SIRS), acid aspiration, trauma (especially with long bone fractures, chest wall injury, lung contusion), multiple emergency transfusions, prolonged hypotension and shock, burn injury, pancreatitis, and post-cardiopulmonary bypass. These clinical conditions may identify a population of patients who are at increased risk of developing acute lung injury; however, there is no definitive test or marker that will signal patients who are at the highest risk for developing the syndrome.

The conventional management of a patient with acute lung injury has primarily been one of support. Despite a multitude of experimental animal studies and human clinical investigational trials, no specific therapy for the prevention or treatment of acute lung injury has yet been identified. At the present time, the only specific therapy is the identification and prompt treatment of the underlying pre-disposing cause of the lung injury.

It appears that the ventilatory management strategy may have a direct impact on the outcome of patients with ARDS. However, there is still a significant mortality despite this improvement with ventilatory management. Alternative therapies are necessary.

New approaches to management are under evaluation and several have shown promise. The past 30 years has seen a number of clinical trials to evaluate potential treatment strategies for patients with ARDS. Some of these approaches involved new strategies for ventilatory management such as the use of extracorporeal membrane oxygenation (ECMO), high frequency ventilation, low frequency ventilation, permissive hypercapnia, inverse ratio ventilation, airway pressure release ventilation, and even prone ventilation. Other innovative therapies include early high dose corticosteroids, platelet activating factor antagonists, prostaglandin E1, inhaled nitric oxide, surfactant replacement therapy, antioxidant therapy, partial liquid ventilation, and the use of nonsteroidal anti-inflammatory agents. Despite an improved understanding of the potential pathogenesis and improvements in technology, there has not been a demonstrated benefit attributable to these new treatment strategies.

The most common cause of death in patients with ARDS continues to be from multiple organ failure and recurrent sepsis. Less than 20 percent of patients die because of the inability to adequately oxygenate or ventilate the patient. The complexities of the balance between the pro- and anti-inflammatory processes that encompasses the pathophysiologic response of this injury directs the response from organ dysfunction secondary to an overzealous pro-inflammatory reaction to infectious complications that result from the immune suppression of a predominant anti-inflammatory response.

When infection is present, the lung is a frequent site for the process and may be extremely difficult to diagnose.

SUMMARY

The embodiments herein include compositions and methods to administer a treatment agent to the lungs of patients or as scientific tools to, for example, study the role and metabolism of surfactants in biological systems. In one embodiment, a composition is described that is capable of mimicking the Surfactant Protein B of lung surfactant. In another embodiment, a method is described to increase the compliance of the lungs by introducing a surfactant agent to the lungs including a composition of an exogenous SP-B peptide or construct (e.g., "Mini-B").

In other embodiments, an exogenous surfactant composition described herein may be used as an adjuvant for delivery of other treatment agents. For example, an exogenous surfactant composition may be used to deliver antibiotics, steroids, growth factors, vaccine, hormones, etc. to the lung. In another example, an exogenous surfactant composition may be used to deliver genetic material to the lungs for treatment of a condition.

In some embodiments, an exogenous surfactant (alone or as an adjuvant) is delivered via a single volume or a multiple of small volumes to the region. These delivery methods may use imaging of the lung to guide the deposition of the treatment agent to the site of the deficiency such as deposition of the composition via a delivery capsule or particle. In other embodiments directed to the treatment of surfactant deficient conditions or agent delivery, the composition may be introduced via an inhalant or injection.

In another embodiment, a method includes multi-component treatments of the lung including but not limited to the introduction of other existing surfactant treatments.

In one embodiment, the treatments may occur at any time after recognition of a surfactant deficiency condition or other identified condition. In another embodiment, the treatments proposed may occur prior to a surfactant deficient condition or identified condition if an occurrence is suspected to precipitate without treatment.

In a further embodiment, a kit is disclosed. One example of such a kit is a kit including a composition that may be introduced to the lung region directly.

BRIEF DESCRIPTION OF THE DRAWINGS

The following drawings form part of the specification and are included to further demonstrate certain aspects of the claims. The claims may be better understood by reference to one or more of these drawings in combination with the detailed description of specific embodiments presented herein.

FIG. 4A illustrates an example of a structural prediction of a Mini-B SP-B construct or peptide based on similar structures in the Protein Data Bank.

FIG. 4B illustrates an experimental example of a Mini-B construct or peptide residue specific structure determination and deposition of the molecular coordinates in the Protein Data Bank at PDB ID: 1SSZ.

DETAILED DESCRIPTION

Figure 1:
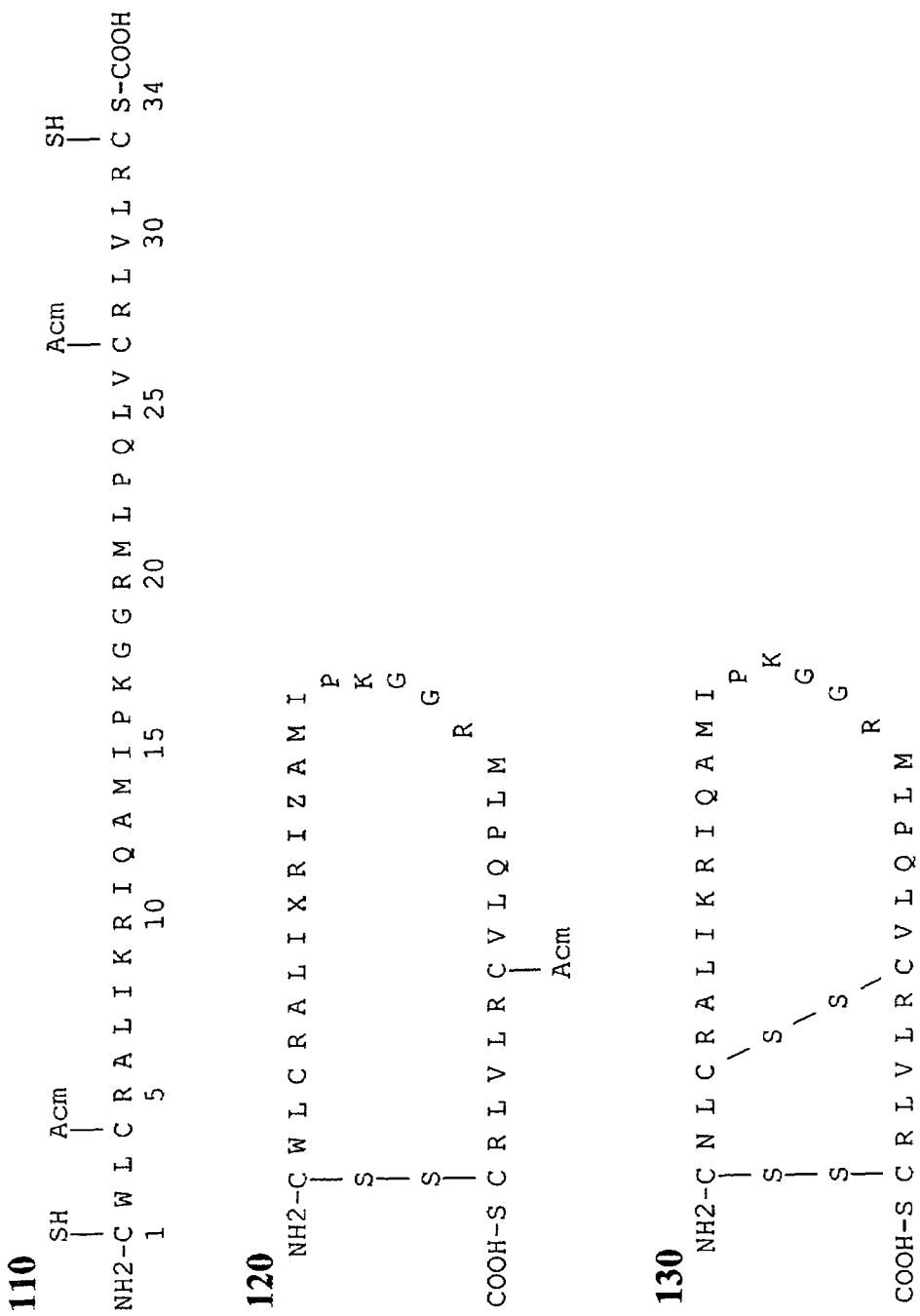
FIG. 1 illustrates one example of a Mini-B construct or peptide and folding into an active conformation.

In one embodiment, a construct or peptide is described that mimics the activity of Surfactant Protein-B (SP-B). In another embodiment, a SP-B-like construct (peptide) referred to herein as "Mini-B construct (or peptide)" may be generated. In yet another embodiment, a composition including a Mini-B construct may be used as a treatment agent to, for example, treat subjects suffering from RDS or ARDS. In still yet another embodiment, a composition including a Mini-B construct as a co-treatment agent with another treatment agent, or as an adjuvant for another treatment agent, may be used in a treatment protocol. In a further embodiment, a Mini-B construct or composition including a Mini-B construct may be used as a scientific tool.

A Mini-B construct (peptide) at the Protein Data Bank is available at the NIH-NSF sponsored Protein Data Bank website and corresponds to accession code: PDB ID: 1SSZ http://www.rcsb.org/pdb/cgi/resultBrowser.cgi?PDBId::PDBId=1SSZ&fromSE=1.

In one embodiment, a Mini-B construct or peptide is a disulfide stabilized 34 residue cyclic construct (peptide) that emulates the in vivo and in vitro structure and activity of a full length 79 residue SP-B native protein in lung surfactant lipid dispersions. A Mini-B construct mimics the N-terminal and C-terminal amphipathic domains of the parent protein that are believed to be the active site of interaction of the protein with surfactant lipids. In one embodiment, a Mini-B construct has the same sequence and disulfide connectivity that constrain the peptide into the active conformation that resembles that of the full length native protein. By folding into this disulfide constrained, native like conformation, the Mini-B construct has a surface charge distribution allowing it to interact with surfactant lipids similar to that of the full length native protein.

The Mini-B constructs described herein are exogenous in the sense that they are derived or developed from outside a body. Examples of exogenous constructs are those derived from synthetic or recombinant techniques. The exogenous constructs tend to have a longer shelf life and are more cost effective than native derived preparations. Further, the exogenous nature of a Mini-B construct minimizes the potential for contamination from viruses or prions that may be associated with native material (e.g., surfactants derived from cow or pig lavage).

The Mini-B constructs described herein have very high activity compared with other currently available surfactant supplements and in combination, for example, with exogenous (e.g., synthetic) surfactant lipids may be formulated to work with a number of lung-related applications such as RDS and the delivery of drugs and/or genetic material.

In one embodiment, Mini-B constructs were designed based on the amino acid sequence and disulfide folded N-terminal and C-terminal linkage observed in human Surfactant Protein-B (SP-B) and most proteins in the saposin family to which lung surfactant proteins belong. Representatively, a Mini-B construct has the same sequence as that observed for residues 8 to 25 of the N-terminal mature protein domain that is jointed to the C-terminal domain of the parent SP-B protein residues 63 to 78 as a single linear 34 residue sequence.

FIG. 1 shows a Mini-B construct as linear peptide with cysteines at positions one and 27 protected (block 110). A Mini-B construct may be synthesized as a single 34 residue linear peptide using conventional FMOC (FastMoc™) synthesis. In one embodiment, a Mini-B construct is derived from two peptides, corresponding to identification codes PDB ID: 1RG3 and PDB ID: 1RG4, in the Protein Data Bank. PDB ID 1 RG3 has the following sequences: $NH_2$-FPIPLPY-CWLCRALIKRIQAMIPKG-COOH. PDB ID 1RG4 has the following amino acid sequence: $NH_2$-GRMLPQLVCRLVL-RCS-COOH. In the embodiment shown in FIG. 1, the N-terminal sequence FPIP (phenylalanine, proline, isoleucine, proline) and the methionine (M) at the C-terminus are not included in a Mini-B construct.

Referring to FIG. 1, four cysteine (Cys) residues are included in the sequence of the construct: Cys-1, Cys-4, Cys-27, and Cys 33. The Cys residues are selectively protected so that Cys-1 and Cys-33 have protecting groups (e.g., trityl (Trt) (not shown)) on the reactive side chains that may be removed by cleavage and deprotection of the peptide from a resin with TFA:phenol:water:ethanedithiol:thioanisole (10: 0.25:0.25:0.25:0.50, v:v). The Cys-4 and Cys-27 groups are protected with a different agent, for example, acetamidomethyl (Acm) to prevent the thiol (SH) side chains from forming a disulfide link. This selective deprotection of the Cys residues promotes air mediated oxidation of Cys residues at positions 1 and 33 in a structure-promoting solvent system including trifluorethanol and buffer to form disulfide bridges between Cys-1 and Cys-33 per se (block 120). After disulfide formation between Cys-1 and Cys-33, the remaining Cys residues are then simultaneously deprotected (e.g., Acm removed with iodine) and oxidized to form a disulfide link between Cys-4 and Cys-27.

In the example described with reference to FIG. 1, directed disulfide formation by selective protection/deprotection of Cys residues inhibits mismatching of disulfide formation between Cys 4 and 33 and Cys 1 and 27 that could lead to an inactive non-native connectivity for the disulfide pairs. The resulting oxidized peptide is purified by conventional preparative scale reverse phase high performance liquid chromatography (HPLC) (Varian Preparative HPLC or similar HPLC) employing a Vydac C8, 2.5×26 cm preparative column and using a linear gradient of water and acetonitrile (0 to 100% acetonitrile in one hour) with 0.1% trifluoroacetic acid as an ion pairing agent to elute the peptide. The molecular mass is verified using matrix assisted laser desorption ionization (MALDI) or electrospray (ESI) mass spectrometry. The resulting N-terminal and C-terminal construct (block 130) has disulfide connectivity that is the same as that observed for the native full length SP-B protein.

The disulfide linkage(s) observed for many of the members of the saposin protein family, serves to constrain the Mini-B construct into a compact amphipathic helix-loop-helix ("helix hairpin") conformation that improves the interaction of the Mini-B construct with surfactant lipids to yield in vitro and in vivo activities similar to those observed for the native full length, 79 residue protein. In vivo and in vitro activity of a Mini-B construct is conserved where the construct has only a single disulfide linkage between Cys-1 and Cys-33. In other words, it has been demonstrated that a second disulfide linkage between Cys4 and Cys-27, when either blocked by a protecting group such as with Acm or mutated to another similar amino acid such as the Cys surrogate (e.g., alanine (Ala)), does not significantly affect the activity of the construct. This suggests that an important element may be the formation of the folded cyclic-like conformation stabilized by the oxidation of the Cys-1 and Cys-33 disulfide linkage. Thus, in another embodiment, a Mini-B construct, has (1) only a single disulfide linkage at Cys-1 and Cys-33 or (2) a disulfide linkage between residue of the C-terminal region of the construct and a residue of the N-terminal region of the construct and either no other disulfide linkage or one or more disulfide linkages that are not between residues across the fold.

In humans, the composition of native lung surfactant is lipid (approximately 90 percent to 97 percent) and various proteins (approximately 10 percent or less) including SP A, B, C, and D. A primary lipid is a phospholipid, principally a phosphatidyl choline (PC) (saturated lipids) and less significantly a phosphatidyl glycerol (PG) (unsaturated lipids). The primary PC lipid is dipalmitoyl phosphatidyl choline (DPPC). The majority of the surfactant lipids are anionic (DPPC is a zwitterion having both positive and negative charges).

The three dimensional structure of native Surfactant Protein B is not yet known. Certain structural properties have been hypothesized including a predominantly amphipathic helical motif of Surfactant Protein B having a cluster of cationic charged amino acid residues in the disulfide linked N-terminal and C-terminal domains of the full length protein. It is believed that the cationic charged amino acids interact with surfactant lipids (e.g., with amionic lipids). A Mini-B construct includes an amphipathic helical motif having a cluster of cationic charged amino acids that folds into a secondary and tertiary structure (including a saposin-like fold) that emulates that predicted for the full length protein. The structurally similar Mini-B construct has in vitro surface activity and emulates mechanistic changes in the molecular topography surfactant lipid dispersions as that observed for the native protein. In vivo activity of the Mini-B construct shows oxygenation and dynamic compliance that compares on a molar basis with the native SP-B protein. However, substitution of polar uncharged residues for cationic residues in the Mini-B construct resulted in a similar structure but greatly attenuated surface activity, altered molecular topography and poor in vivo activity in animal model systems. These findings suggest that the unique charge distribution of the disulfide linked N-terminal and C-terminal domains of SP-B are at least one of the major components for optimal function of the protein in surfactant lipids.

Figure 2:
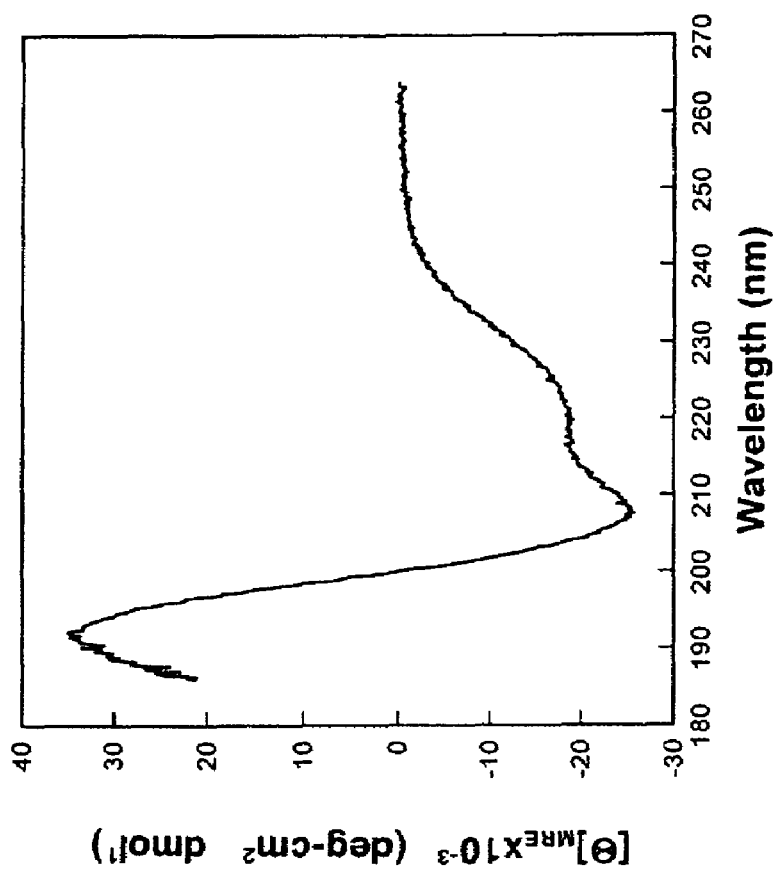
FIG. 2 illustrates an example of a circular dichroism spectrum of a Mini-B construct or peptide in a structure promoting membrane-mimic solvent system of hexafluoroisopropanol (HFIP)-10 mM phosphate buffer.
Figure 3:
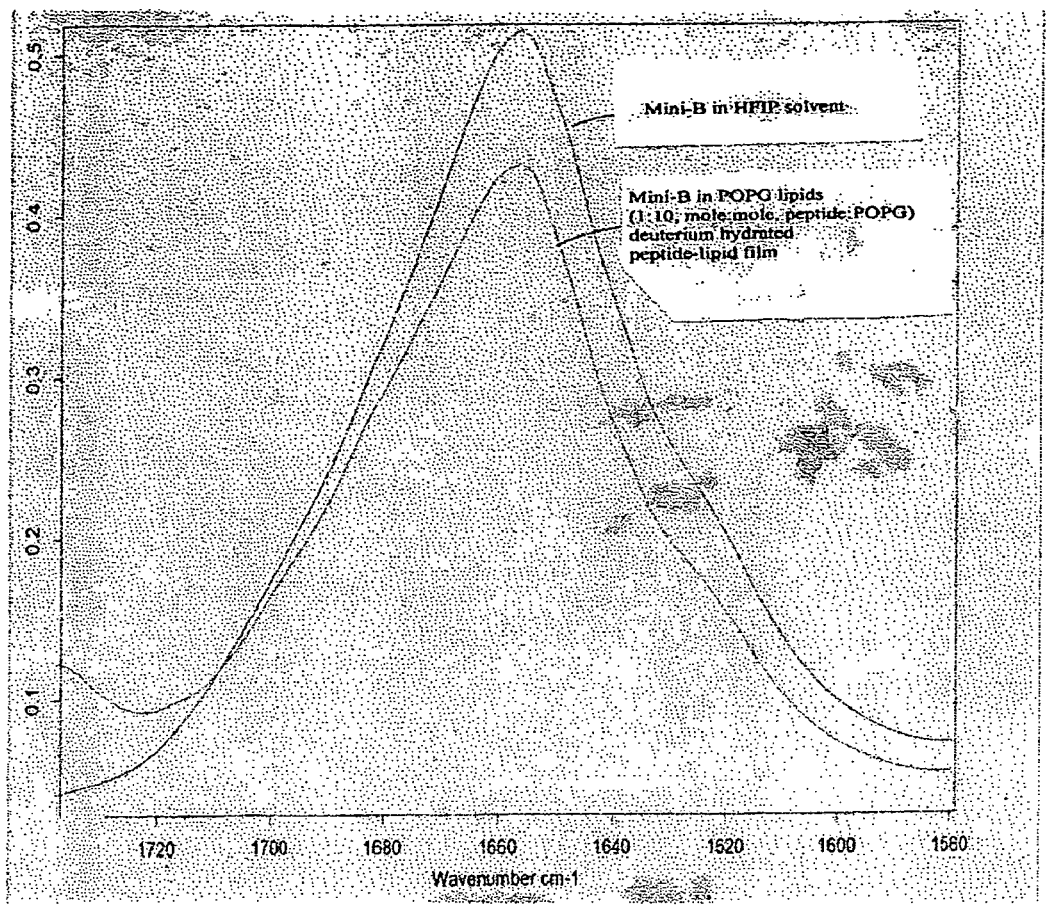
FIG. 3 illustrates an example of Fourier Transform Infrared spectra of a Mini-B construct or peptide in either HFIP-IO mM phosphate buffer or 1-palmitoyl-2-oleoyl phosphatidylglycerol lipids for comparison with secondary structures observed with circular dichroism measurements of FIG. 2.

The overall secondary structure of a Mini-B construct has been examined using Circular Dichroism (CD) and Fourier Transform Infrared (FTR) (FIG. 2 and FIG. 3). For example, in the structure promoting solvent system of hexafluoroisopropanol (HFIP)-buffer that is similar to the environment of surfactant lipid systems, a dominant alpha helical conformation is formed with lesser contributions from turn-loop, beta sheet, and disordered structures. FIG. 2 represents a typical spectrum of a Mini-B construct that has a dominant alpha helical conformation with dichroic minima at 222 and 208 nanometers and a dichroic maximum near 193 nm. Computer analysis of the spectrum with the CD analysis SELCON 3™ indicates the helical component is approximately 50 percent of the conformation for the construct in this solvent.

FIG. 3 shows an FTR analysis that further confirms the secondary structures observed with circular dichroism measurements of FIG. 2. In HFIP, the amide I band shows strong absorbance in the 1662 cm−1 to 1648 cm−1 region with a peak at 1656 cm−1 typical of dominant alpha helical conformation. There are also shoulders in the 1643 cm−1 and 1630 cm−1 ranges typical of random and beta sheet conformations. Similar spectra are observed for a Mini-B construct in palmityl-oleyl phosphatidyl phosphoglycerol (POPG), a typical anionic phospholipid lipid found in lung surfactant that is known to associate with cationic surfactant peptides. This suggests that a Mini-B construct assumes similar dominant alpha helical conformation in HFIP and in surfactant lipids used as components of dispersions for treatment of RDS. Examination of the Mini-B construct in surfactant lipid dispersions used for treatment of RDS with FTIR further indicates that the Mini-B construct includes a dominant helical conformation with minor contributions from turn, beta sheet and disordered structures.

The structure of a Mini-B construct presented here was resolved using isotope enhanced FTIR. Based on experimental data, the molecular coordinate set was refined using molecular dynamics and mechanics in the Insight II environment with the CHARMM™ force field (a scientifically accepted software package used to refine experimental data to solve a three dimensional structure of a protein).

Figure 5:
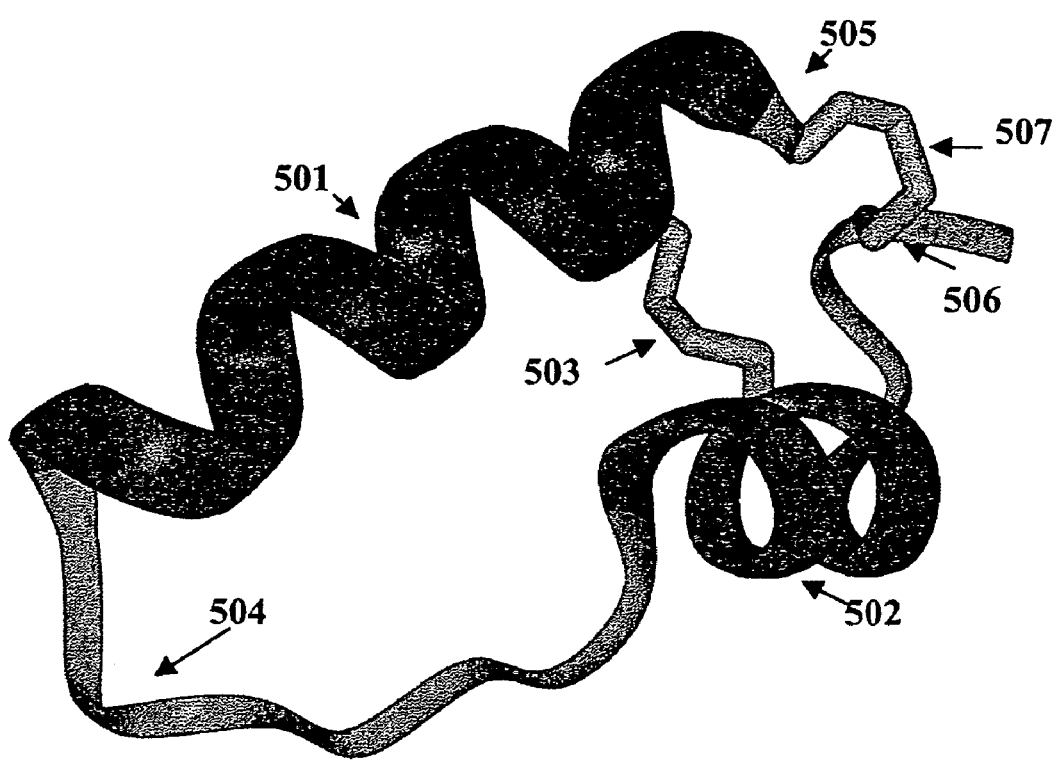
FIG. 5 illustrates an example of a ribbon representation of a Mini-B construct or peptide (PDB ID: 1SSZ).

The overall conformational estimates of a Mini-B construct from CD and FTIR compare well with those percentages determined by predictive neural network algorithms (e.g., Predict Protein, http://cubic.bioc.columbia.edu/predictprotein/) based on the crystal (Saposin B, PDB ID: 1N69), NMR structures (NK-Lysin, PDB ID: 1NKL; Saposin C, PBD ID:1M12), and the isotope enhanced structure for the N-terminal segment of SP-B in surfactant lipids (SP-B1-25, PDB ID: 1DFW). Based on structural data and known structures from the Protein Data Bank, a proposed structure for the Mini-B construct is shown in FIG. 4A. Preliminary predictions have been confirmed by solving the Mini-B structure using isotope edited Mini-B peptides and FTIR (FIG. 4B) and ribbon representation of a Mini-B construct with representative residue specific conformations and folding of the peptide structure (FIG. 5).

Helical domains were predicted for a Mini-B construct and reveal the presence of an anti-parallel sheet in the mid-sequence bend domain (FIG. 4B). This mid sequence with beta sheet propensity allows a Mini-B construct to self-associate with other Mini-B constructs by hydrogen bonding to an adjacent Mini-B construct forming a stable anti-parallel beta sheet structure. In one embodiment, a monomeric composition of a Mini-B construct may be used. In another embodiment, a bond such as a hydrogen bond may be used to generate dimeric to multimeric compositions of a Mini-B construct. Any one or more of these compositions may be used to generate a surfactant composition. In another embodiment, any one or combination of these compositions may be used to generate an agent capable of targeting therapies to the lungs, for example, antibiotic or other drug, steroid, genetic material treatments by, for example, combining the agent with a Mini-B construct.

Molecular modeling of secondary structure assignments templated on Protein Data Bank structures of SP-B1-25(PDB ID: 1DFW) and NK-Lysin (PDB ID: 1NKL) and SAPOSIN B (PDB ID: 1N69) were conducted by molecular dynamics and energy minimization to optimize the protein structure geometry. The results of modeling reveal 15 helical residues or 15/34=44% helix, 8 to 10 random residues or 10/34=29 random, 5 loop or turn residues or 5/34=15% turn.

The optimized structure indicates that the amount and location of helical structure elements is similar to that observed from the experimental measurements of the peptide using CD and FTIR techniques. Predicted secondary structural assignments of the amino acid sequence for a Mini-B construct were based on the neural network Predict Protein program, Ph.D.

Isotope enhanced 13C carbonyl labeling of the amino acid residues in the N-terminal, mid, and C-terminal segments of the construct confirmed the residue specific helical elements in the N- and C-terminal domains and assigned turn and beta sheet elements to the mid-sequence. This structure in turn gives the correctly folded peptide a surface charge distribution that is similar to native SP-B lipid interaction domain that improves the surfactant lipid interaction function.

FIG. 5 shows a ribbon representation of a Mini-B construct (PDB ID: 1SSZ) illustrating the tertiary structure of the construct. In this embodiment, a Mini-B construct has an N-terminal helical domain (top of illustration 501) and a C-terminal helical domain (lower part of illustration, 502) are connected by disulfide linkages 503 and 507. The middle loop sequence between the two helical termini includes turn 504 and an anti-parallel beta sheet and a random segment at the N-terminus 505 and C-terminus 506.

In one embodiment, a composition including a SP-B-like construct (e.g., a Mini-B construct) may be used to target delivery of the SP-B mimic or another agent to the lungs of a subject. In another embodiment, a composition including at least one SP-B-like construct (e.g., a Mini-B construct) may be used to target delivery to the lungs of a subject with RDS (or ARDS). One delivery mechanism is via an inhalable composition. An inhalable composition may include a liquid such as a fine mist or dry powder where the composition is encapsulated or free-flowing. The encapsulated composition may include one or more lipids (e.g., phospholipids) and/or other peptides and/or proteins necessary to treat a condition such as a lung condition including asthma.

As noted above, a composition including a Mini-B construct may be combined with lipid(s). Representatively, such lipid(s) may be of the type that are associated with lung surfactant. In one embodiment, a synthetic lipid dispersion was developed that mimics native surfactant lipid. In one embodiment used in Examples 1-3 herein, the dispersion ("ISPL") includes 35 mg lipids/ml 150 mM phosphate buffer saline solution (16 mg/ml dipalmitoyl phosphatidyl choline (DPPC), 10 mg/ml palmitoyl-oleoyl phosphatidyl choline (POPC), 3 mg/ml palmitoyl-oleoyl phosphatidyl glycerol (POPG), 1 mg/ml palmitoyl-oleoyl phosphatidyl ethanolamine (POPE), 3 mg/ml palmitoyl-oleoyl phosphatidyl serine (POPS), and 2 mg/ml cholesterol). ISPL simulates the native cow/calf lipid dispersion of INFASURF™.

A composition including a Mini-B construct may also serve as an adjuvant and may accompany a therapeutic agent. In this manner, the lung may serve as a conduit to deliver drugs (e.g., antibiotics), growth factors (e.g., fibroblast growth factor (FGF), erythropoietin (EPO)) or other biomolecules (e.g., peptides, proteins), vaccines, hormones (e.g., insulin), etc. to the systemic circulation. One advantage to this conduit is that the vascular network associated with the lungs may provide rapid systemic delivery of a treatment agent. A Mini-B construct functions similar to native surfactant B and thus can provide access, perhaps in the presence of a lipid (e.g., a synthetic phospholipid), of a treatment agent to the lungs. In one example, a composition such as a composition including a Mini-B construct may coat the outside of a microsphere carrying a treatment agent (thus directing the composition to the lung inner surface). In another example, a composition including a Mini-B construct may be harbored within a delivery vehicle such as a microparticle and then released at a predetermined rate during or after delivery has occurred for the composition.

In another embodiment, a composition containing at least one SP-B-like construct (e.g., a Mini-B construct) may be used to target meconium aspiration syndrome (MAS) in full-term newborns. MAS is a consequence of improperly expelled waste products from the gastro-intestinal tact that may occupy a newborn subject's lungs at birth, causing breathing difficulties. This disorder is characterized by the presence in the lungs of meconium, inflammatory cells, inflammatory mediators, edema fluid, protein and other debris. Inhaled meconium can inactivate a newborn's own natural surfactant.

As noted above, surfactant supplements are known. INFASURF™ (calfactant) is an intratracheal, non-pyrogenic lung surfactant supplement intended primarily for intratracheal instillations. It includes an extract of natural surfactant from calf lungs that includes phopholipids, neutral lipids, and hydrophobic surfactant-associated proteins B and C. In another embodiment, a composition including a Mini-B construct may be used in conjunction with a surfactant supplement such as INFASURF™, either in a combined composition or consecutively administered compositions. A representative treatment is for RDS and ARDS.

An embodiment of a Mini-B construct may also serve as a scientific tool. Representatively, a Mini-B construct may be used to study the role and metabolism of surfactants in biological systems.

In still further embodiments, any of the embodiments of a Mini-B construct described may form a portion of a surfactant replacement or supplement kit for use with the methods described above. As the encoded proteins or peptides may be employed to treat a condition and the corresponding peptides may be employed to replace missing components or deliver an agent. The kits will thus comprise, a suitable container means, a peptide (e.g., a Mini-B construct), and/or an agent (e.g., antibiotic, genetic material). In other embodiments, the Mini-B construct may be combined with any other known therapy such as oxygen supplements or anti-inflammatory agents.

The kits may further include suitable aliquots of a construct composition for administration. These aliquots may include daily amounts for a single dose or multiple dose aliquot package separately for administration several times daily.

Suitable containers of the kits will generally include at least one vial, test tube, flask, bottle, syringe or other container, into which the construct composition may be placed, and preferably, suitably aliquoted. Where a second or third component (e.g., treatment agent) is provided, the kit will also generally contain a second, third or other additional container into which the component may be placed. The kits will also typically include a container for the construct composition, and any other component containers in close confinement for commercial sale. Such containers may include injection or blow-molded plastic containers into which the desired vials are retained.

Table I shows the similarity between a Mini-B construct and various other known SP-B sequences (taken from the ExPASy Molecular Biology Server: Swiss-Prot and TrEMBL:http://us.expasy.org/cgi-bin/sprot-search-de?Surfactant%20Protein%20B. Mini-B construct sequences are bolded from the full length sequence for clarity.

TABLE I

>sp|P07988|PSPB_HUMAN Pulmonary surfactant-associated protein B precursor (SP-B) (6 kDa protein) (Pulmonary surfactant-associated proteolipid SPL(Phe)) (18 kDa pulmonary-surfactant protein) - *Homo sapiens* (Human).
FPIPLPYCWLCRALIKRIQAMIPKGALAVAVAQVCRVVPLVAGGI CQCLAERYSVILLDTLLGRMLPQLVCRLVLRCSM
>sp|P15781|PSPB_BOVIN Pulmonary surfactant-associated protein B (SP-B) (6 kDa protein) (Pulmonary surfactant-associated proteolipid SPL(Phe)) - *Bos taurus* (Bovine).
FPIPIPYCWLLRTLIKKIQAVIPKGVLAMTVAQVCHVVPLLVGGIIQQ LVIEYSVILXTDTLLGRLPNLVCGLRLRCSG
>sp|P17129|PSPB_CANFA Pulmonary surfactant-associated protein B precursor (SP-B) (6 kDa protein) (Pulmonary surfactant-associated proteolipid SPL(Phe)) (Pulmonary surfactant protein 18) (SP 18) (Fragment) - *Canis familiaris* (Dog).
LPIPLPYCWLCRTLIKRIQAMIPKGV-LAVTVGQVCHVVPLVVGGICQ CLGERYTVLLLDALLGRMLPQLVCGLVLRCSH
>sp|P50405|PSPB_MOUSE Pulmonary surfactant-associated protein B precursor (SP-B) (Pulmonary surfactant-associated proteolipid SPL(Phe)) - *Mus musculus* (Mouse).
LPIPLPFCWLCRTLIKRVQAVIPKGVLAVAVSQVCHVVPLVVGGI CQCLAERYTVLLLDALLGRVVPQLVCGLVLRCST
>sp|P15782|PSPB_PIG Pulmonary surfactant-associated protein B (SP-B) (8 kDa protein) (Pulmonary surfactant-associated proteolipid SPL(Phe)) - *Sus scrofa* (Pig).
FPIPLPFCWLCRTLIKRIQAVVPKGVLLKAVAQVCHVVPLPVGGI CQCLAERYIVICLNMLLDRTLPQLVCGLVLRCSS
>sp|P15285|PSPB_RABIT Pulmonary surfactant-associated protein B precursor (SP-B) (6 kDa protein) (Pulmonary surfactant-associated proteolipid SPL(Phe)) - *Oryctolagus cuniculus* (Rabbit).
FPIPLPLCWLCRTLLKRIQAMIPKGVLAMAVAQVCHVVPLVVGGI CQCLAERYTVILLEVLLGHVLPQLVCGLVLRCSS
>sp|P22355|PSPB_RAT Pulmonary surfactant-associated protein B precursor (SP-B) (Pulmonary surfactant-associated proteolipid SPL(Phe)) - *Rattus norvegicus* (Rat).
LPIPLPFCWLCRTLIKRVQAVIPKGVLAVAVSQVCHVVPLVVGGI CQCLAERYTVLLLDALLGRVVPQLVCGLVLRCST
>tr|O35489 Surfactant protein-B - *Cavia porcellus* (Guinea pig).
FPIPLPYCRLCKTLLKRVQAMIPKGVLAMAVAQVCHVVPLVAGGI CQCLAERYTVLLLDALLSHLLPQLVCGLVLRCSM
>tr|Q9BDZ9 Pulmonary surfactant-associated protein B precursor (Fragment) - *Ovis aries* (Sheep).
FPIPLPFCWLCRTLIKRIQAVIPKGVLAMTVAQVCHVVPLLVGGI CQCLVERYSVILLDTLLGRMLPQLVCGLVLRCSS

TABLE I-continued

>tr|Q7YRF0 Pulmonary surfactant-associated protein B (Fragment) - *Equus caballus* (Horse).
QVCHVVPLVVGGICQCLAERYTVILLDALLGRFVPQLVCGLV LRCSS Table II shows a Mini-B construct compared to various species. Comparison of sequences between species shows that the amino acid sequences are highly conserved with few substitutions. Most substitutions are very conservative (amino acid substitutions underlined).

TABLE II

| | |
|---|---|
| Human(Mini-B): | CWLCRALIKRIQAMIPKGGRMLPQLVCRLVLRCS |
| Bovine (Cow): | CWLLRTLIKKIQAVIPKGGR_LPNLVCGLRLRCS |
| Porcine (Pig): | CWLCRTLIKRIQAVVPKGDRTLPQLVCGLVLRCS |
| Ovine (Sheep): | CWLCRTLIKRIQAVIPKGGRMLPQLVCGLVLRCS |
| Rat: | CWLCRTLIKRVQAVIPKGGRVVPQLVCGLVLRCS |
| Mouse: | CWLCRTLIKRVQAVIPKGGRVVPQLVCGLVLRCS |
| Guinea pig: | CRLCKTLLKRVQAMIPKGSHLLPQLVCGLVLRCS |
| Rabbit: | CWLCRTLLKRIQAMIPKGGHVLPQLVCGLVLRCS |
| Dog: | CWLCRTLIKRIQAMIPKGGRMLPQLVCGLVLRCS |
| Horse(fragment): | GRFVPQLVCGLVLRCS |

EXAMPLES

Example 1

Figures 6A, 6B:
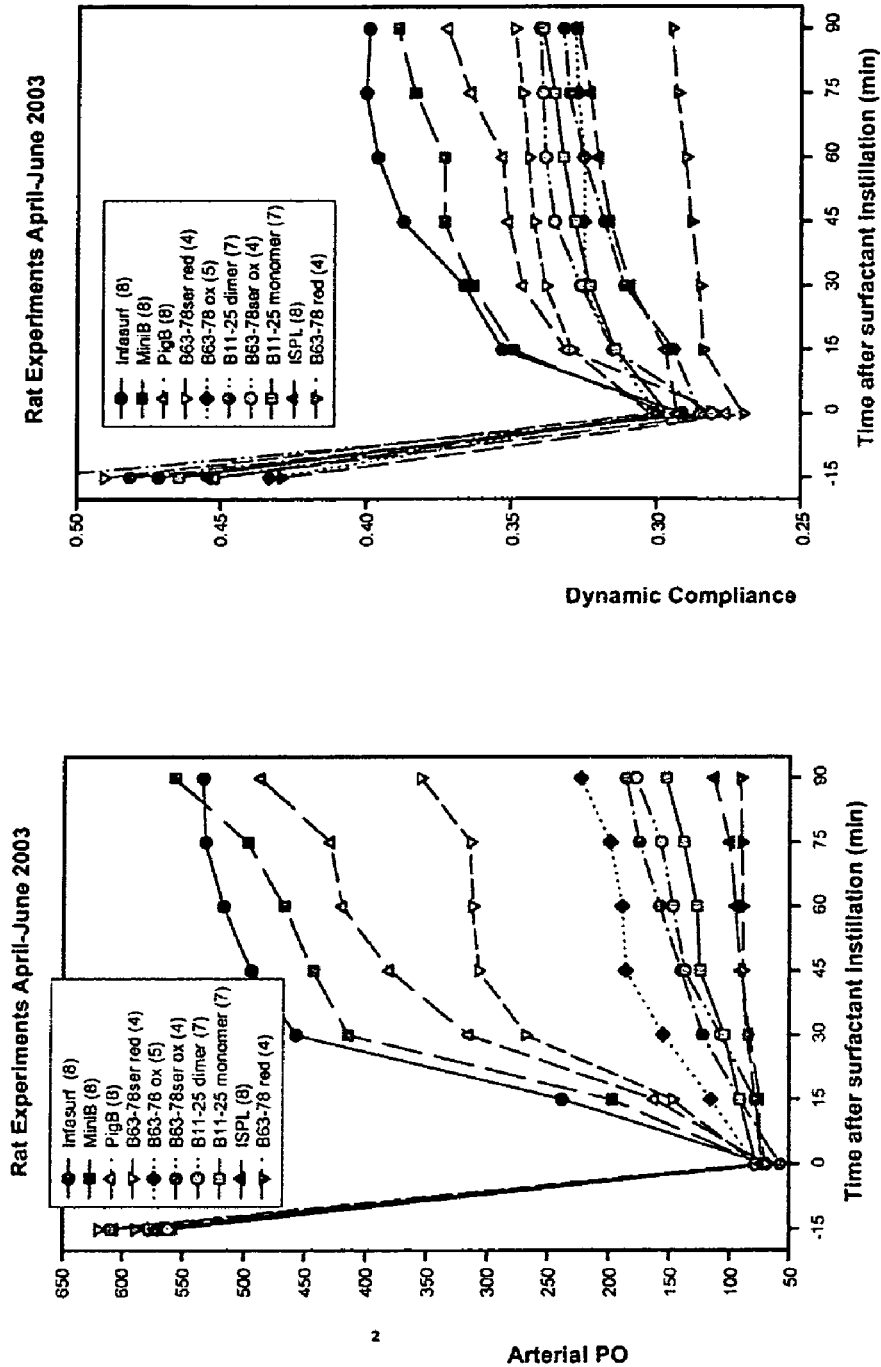
FIG. 6A represents an oxygenation response of lavaged rat model of RDS comparing a known exogenous surfactant, INFASURF™ replacement formulation, pig native surfactant B in INFASURF™ lipids, a Mini-B construct or peptide in simulated INFASURF™ lipids, the C-terminal domain of SP-B (residues 63-78) in the oxidized and reduced format, the N-terminal domain of SP-B (residues 11 to 25 of native SP-B) in the monomer and dimer conformation and simulated INFASURF™ lipids alone.
FIG. 6B represents a dynamic compliance measurements in the Rat RDS animal model system comparing a known exogenous surfactant, INFASURF™, pig native surfactant B in INFASURF™ lipids, a Mini-B construct or peptide in simulated INFASURF™ lipids, the C-terminal domain of SP-B (residues 63-78) in the oxidized and reduced format, the N-terminal domain of SP-B (residues 11 to 25 of native SP-B) in the monomer and dimer conformation and simulated INFASURF™ lipids alone.

FIG. 6A illustrates an example of an oxygenation response of a lavaged rat model of RDS comparing INFASURF™, a known effective animal based (cow lung lavage that includes surfactant lipids and native Cow SP-B and SP—C proteins) supplement formulation (—O—), pig native surfactant B in INFASURF™ lipids (—▲—), Mini-B peptide in simulated INFASURF™ lipids (—■—), the C-terminal domain of SP-B (residues 63-78) in the oxidized (--♦--) and reduced format (—∇--), a serine derivative the C-terminal domain of SP-B (residues 63-78) with cationic arginines (R) replaced with serine residues, in oxidized (—O--) and (—∇—) format, the N-terminal domain of SP-B (residues 11 to 25 of native SP-B) in the monomer (—□—) and a dimer (—●--) conformation and ISPL alone (—Δ—). The results suggest that the full length of a Mini-B construct of FIG. 5 outperforms all of the peptide segments of Mini-B separately. The activity of Mini-B construct closely parallels the oxygenation response that is observed for full-length native SP-B protein (residues 1 to 79). A Mini-B construct also compares favorably with the commercial preparation INFASURF™ that contains both the native SP-B and SP—C protein.

Example 2

FIG. 6B represents dynamic compliance measurements (a measure of lung mechanical plasticity) in the Rat RDS animal model system comparing INFASURF™ replacement formulation, pig native surfactant B in INFASURF™ lipids (—O—), a Mini-B construct in simulated INFASURF™ lipids (—■—), the C-terminal domain of SP-B (residues 63-78) in the oxidized (--♦--) and reduced (—∇--) format, a serine derivative the C-terminal domain of SP-B (residues 63-78) with cationic arginines (R) replaced with serine residues, in oxidized (—O--) and (—∇—) format, the N-terminal domain of SP-B (residues 11 to 25 of native SP-B) in the monomer (—□—) and dimer (—●--) conformation and ISPL alone (—Δ—). The results indicate that a Mini-B construct performs very nearly as well as the commercial preparation containing both native SP-B and SP—C proteins and out performs all other formulations including native SP-B and peptide elements of the N- and C-terminal domains of the oxidized Mini-B construct.

The in vivo activity of Mini-B in the rat RDS model system exceeds that observed for native pig SP-B in synthetic surfactant lipids (FIGS. 6A and 6B). The activity of a Mini-B construct is very similar to that of the commercial preparation INFASURF™ that includes equimolar amounts of native SP-B in native lung surfactant lipids and native SP—C proteins typically used in present RDS therapies. It is of interest that the two peptides that comprise elements of the Mini-B construct, B11-25 and B63-78 have relatively ineffective in vivo activity compared with a Mini-B construct, native pig SP-B and INFASURF™ formulations.

Example 3

Further in vitro surface activity studies of a Mini-B construct in vitro surface activity using Langmuir trough and surface pressure dependent changes in peptide-lipid film microstructure also suggest that a Mini-B construct has a mechanism of action similar to that of the native SP-B protein.

Figure 7:
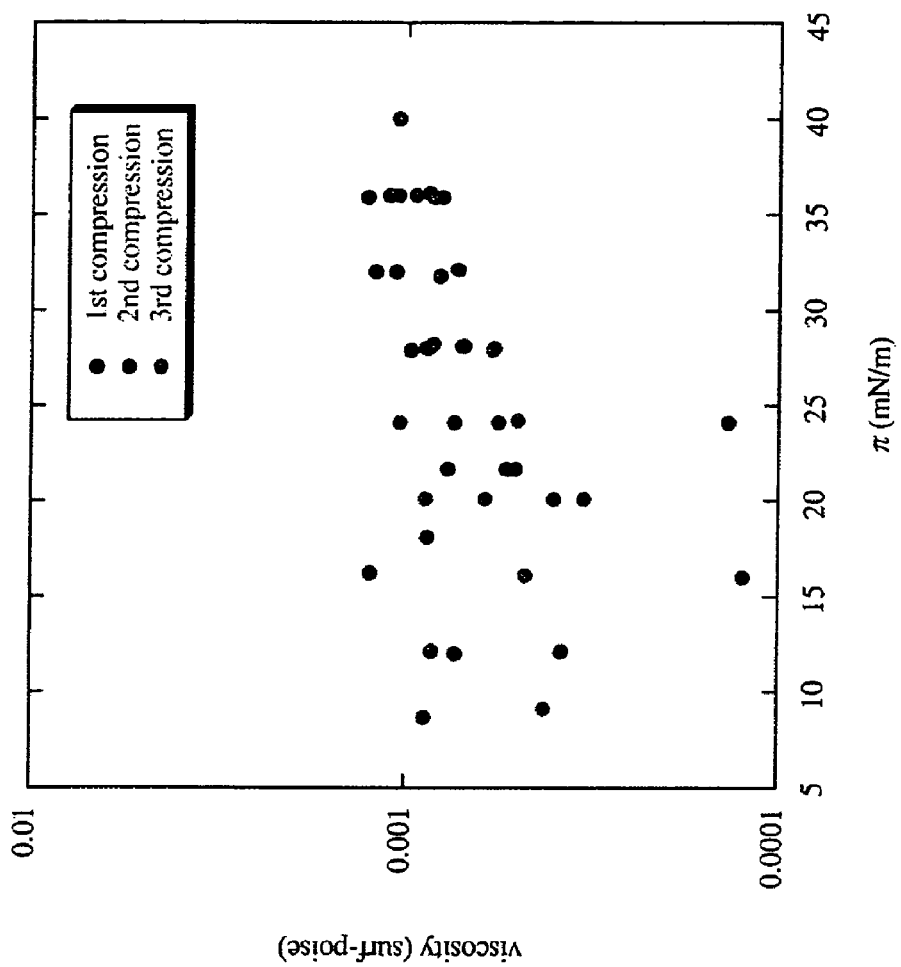
FIG. 7 illustrates an example of the surface shear viscosity of Mini-B construct or peptide in simulated INFASURFM™ lipids.

Surface shear viscosity measurements of a Mini-B construct in a simulated INFASURF™ lipid dispersion ISPL (cow lung lavage lipids) is represented in FIG. 7. The shear surface viscosity remains constant at a large range of surface pressures and over compression-expansion cycles (film collapsed at the end of each compression). The film remains liquid-like at any surface pressure suggesting that the surface viscosity of a Mini-B construct in ISPL lipids is similar to that observed in surfactant preparations containing native SP-B and SP—C proteins and lipids.

Figure 8:
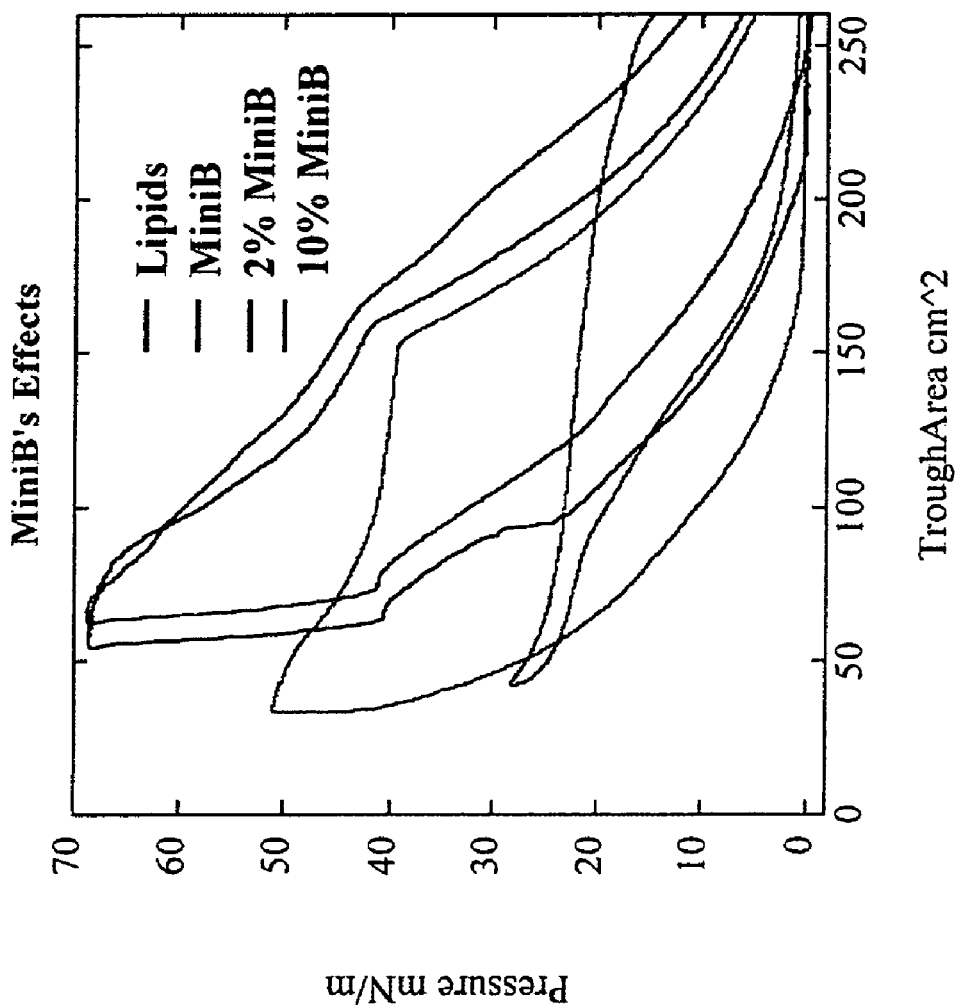
FIG. 8 illustrates an example of the effects of a Mini-B construct in the presence of several different materials to maintain a particular substance at an interface.

Langmuir trough measurements of a Mini-B construct in ISPL lipids are represented in FIG. 8. The peptide at two different concentrations is compared to lipids with any peptide. Lipids alone on the Langmuir trough show very little change in surface pressure with compression of the air-water interface film. However, addition of even small amounts of a Mini-B construct enhances the surface activity resulting in increased surface pressure as a function of compression of the film (decreased trough area) followed by regular hysteretic pressure changes upon film decompression. Higher concentrations of a Mini-B construct in the lipids further enhance the surface activity of the preparation and show the characteristic chances in surface pressure as a function of compression/decompression of the lipid-peptide surface film that are associated with optimal in vitro activity typical of lung surfactant preparations containing SP-B native protein.

Figure 9:
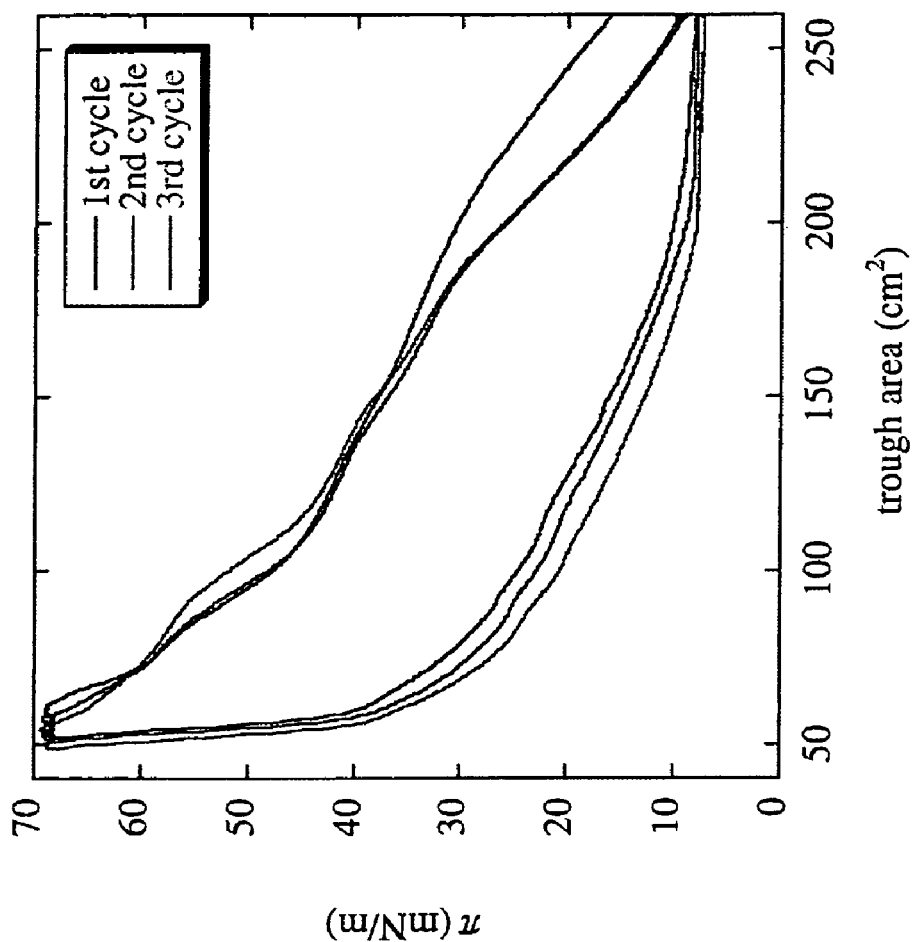
FIG. 9 illustrates an example of Langmuir trough measurements of a Mini-B construct or peptide in synthetic surfactant cow lung lipids and testing the mixture as a potential lung surfactant by measuring collapse and respreading.

FIG. 9 illustrates Langmuir trough measurements of a Mini-B construct in ISPL. The construct was measured at a single concentration to show the consistent pressure dependent reproducibility of the construct in the lipids that is an important criteria of an effective lung surfactant dispersion. Lipids alone on the Langmuir trough show very little change in surface pressure with compression of the air-water interface film. However, addition of even small amounts of a Mini-B construct enhances the surface activity resulting in increased surface pressure as a function of compression of the film (decreased trough area) followed by regular hysteretic pressure changes upon film decompression. Higher concentrations of a Mini-B construct in the lipids further enhance the surface activity of the preparation and show the characteristic changes in surface pressure as a function of compression/decompression of the lipid-peptide surface film that are associated with optimal in vitro activity typical of lung surfactant preparations containing SP-B native protein.

Figure 11:
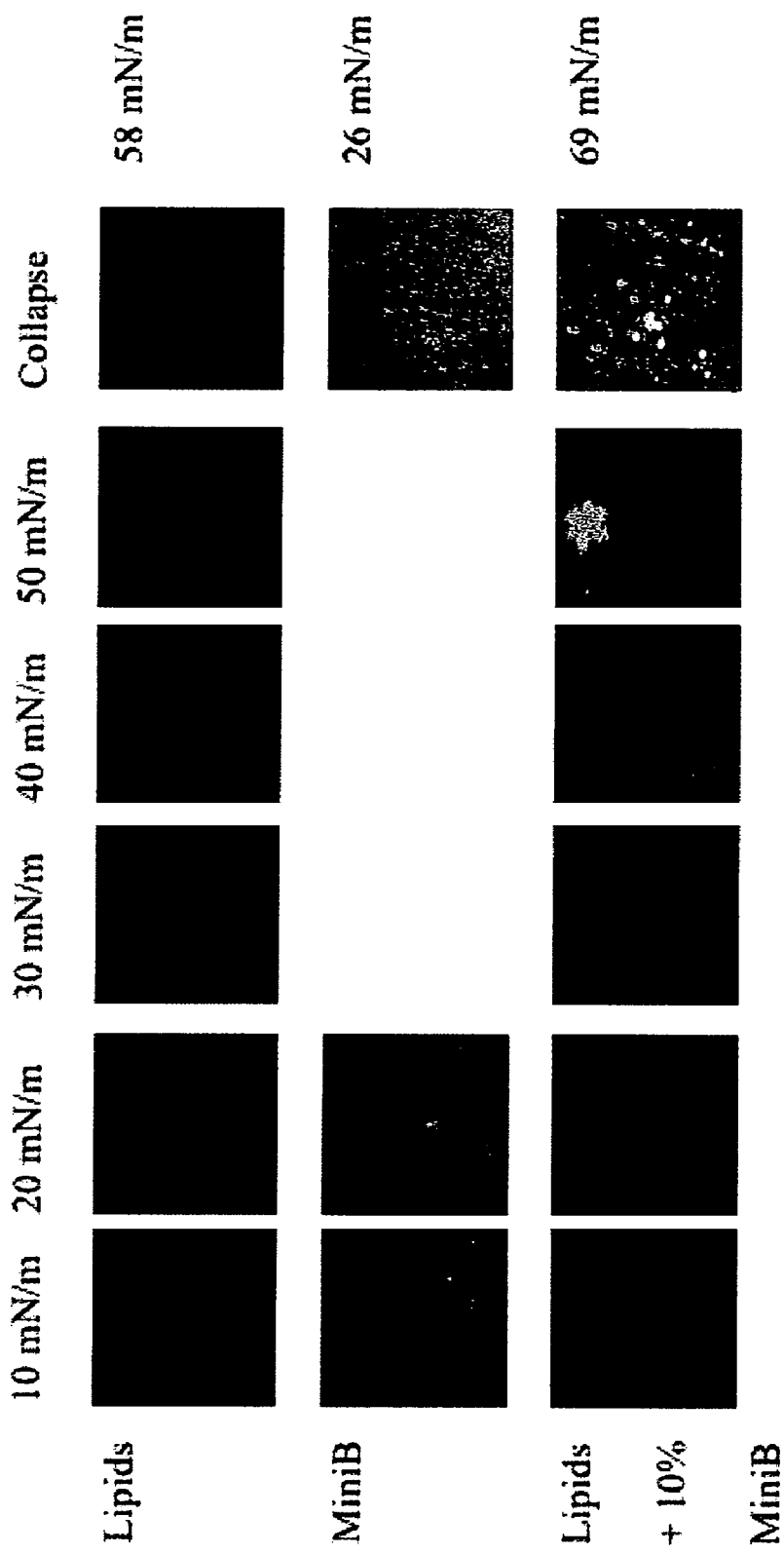
FIG. 11 represents Brewster Angle Microscopes (BAM) images of monolayer surfaces of a Mini-B construct or peptide in simulated cow lung phospholipids versus lipids alone on the Langmuir trough as a function of surface pressure.

Brewster Angle Microscope images of monolayer surfaces of Mini-B-ISPL lipids versus lipids alone on the Langmuir trough as a function of surface pressure is represented in FIG. 11. Preparations containing Mini-B-lipids aggregate while lipids alone do not. This Mini-B induced lipid aggregation in monolayers is typical of the effect of native surfactant protein B and surfactant B type peptides.

Figure 12:
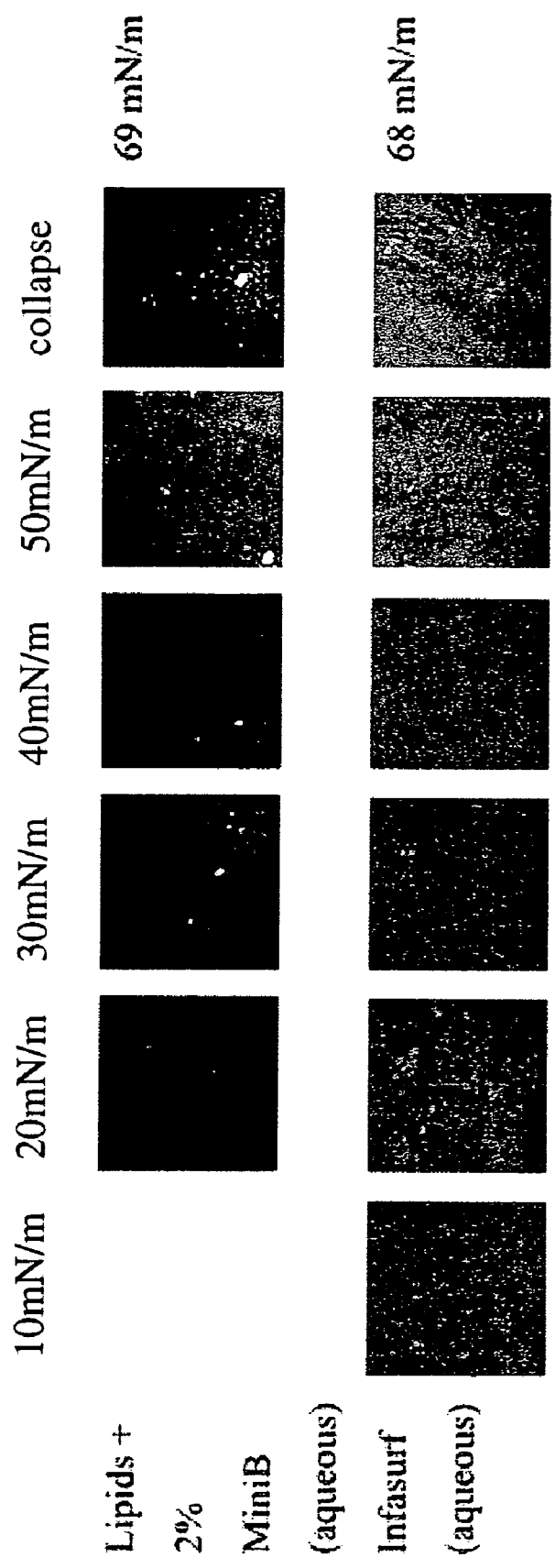
FIG. 12 Brewster Angle Microscope Images (BAM) of monolayer surfaces of a Mini-B construct or peptide in simulated cow lung phospholipids compared with a commercial surfactant preparation, INFASURF™.

Brewster Angle Microscope images of monlayer surfaces of Mini-B-synthetic cow lung lipids compared with the commercial surfactant preparation INFASURF™ that contains native SP-B and SP-C proteins is represented in FIG. 12. Preparations containing Mini-B aggregate lipids were similar to the commercial surfactant preparation. This peptide induced change in surface lipid ordering suggests that the mechanism of action of a Mini-B construct closely resembles that of the native SP-B protein.

Figure 10:
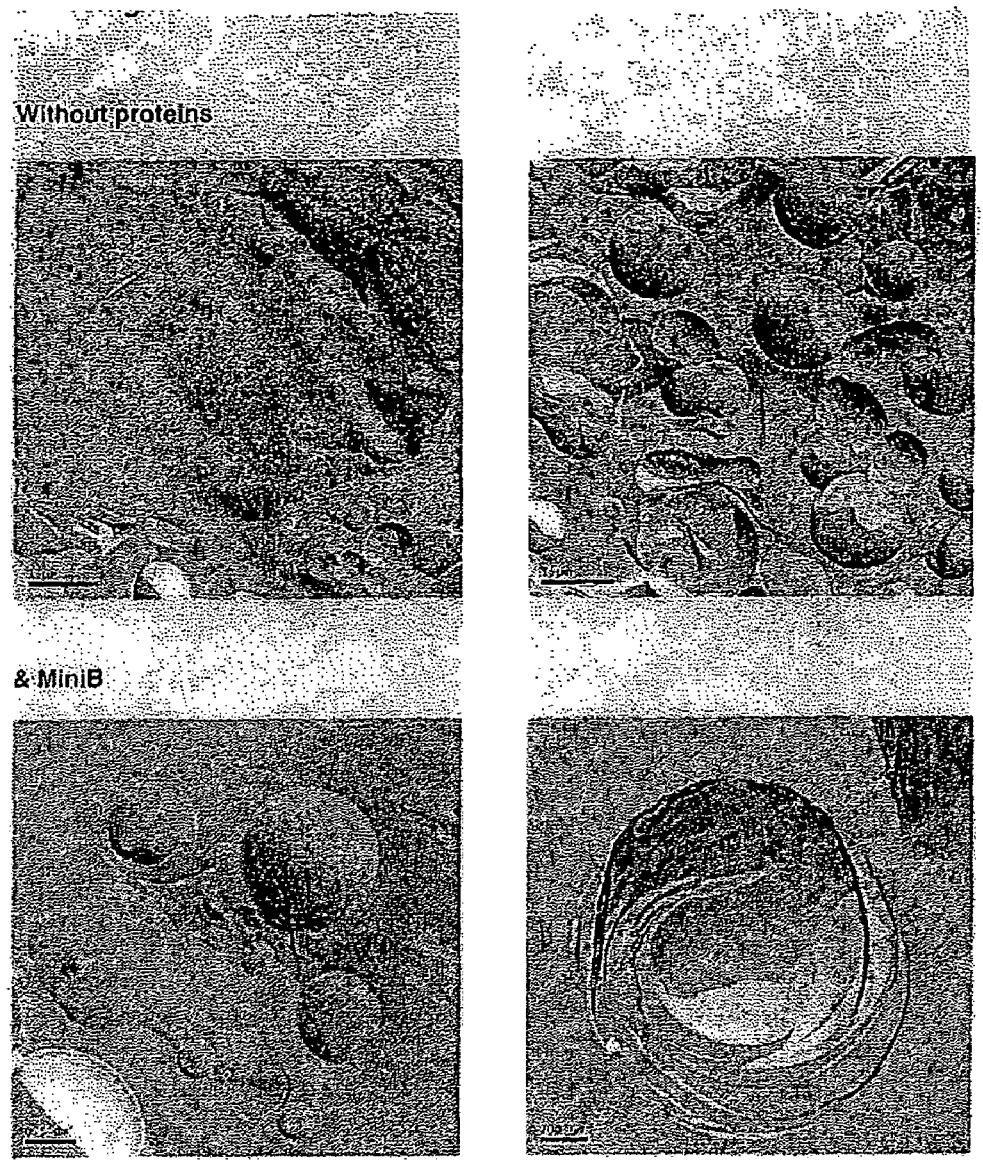
FIG. 10 illustrates scanning electron micrographs of dispersions of simulated cow lung phospholipids with and without a Mini-B construct or a peptide.

Studies of the surface film isotherms of a Mini-B construct, native SP-B and commercial preparations of native proteins and lipids have very similar compression and respreading properties. Scanning electron micrographs of dispersions of simulated cow lung surfactant lipids used in in vitro and in vivo experiments in this application show specific morphological changes with the addition of a Mini-B construct (FIG. 10). The simulated cow lung surfactant lipids (ISPL) without peptide consist of flat sheets with some vesicles of one to two microns (μm) in diameter (top of FIG. 10). In contrast simulated cow lung surfactant lipids with a Mini-B construct have many multi-vesicular liposomes that are similar to the morphology and size distribution of the microstructure observed in most commercial preparations containing native SP-B protein. Similarly, the hysteretic formation and collapse cycles of nano-structures (see Brewster Angle Microscope images, "BAM images" FIGS. 11 and 12) observed for native SP-B and other native lipid-protein preparations indicates that a Mini-B construct functions similarly to that of native full-length SP-B protein. A summary comparing the performance of natural lung surfactant supplements surface activity with regard to the highest surface pressure upon compression ($\pi_c$) on the Langmuir trough and respreading ratio (RR) is shown in Table III. A Mini-B construct containing simulated cow surfactant lipids compare very favorably with those of commercial lung surfactant supplements containing native SP-B protein from animal sources.

TABLE III

Natural lung surfactant performances

|  | $\pi_c$ (mN/m) | RR (%) |
|---|---|---|
| Survanta | 66.0 | 84.03 |
| Curosurf | 70.7 | 89.1 |
| Infasurf | 68.0 | 93.6 |
| Native Pig LS | 70.7 | 91.4 |
| Infa-MiniB | 68.6 | 97.0 |

FIG. 10 represents scanning electron micrographs of dispersions of simulated cow lung lipids (ISPL). Top micrographs show example of the lipids alone with no peptide. Lower micrographs show simulated cow lung surfactant lipids with a Mini-B construct. Scanning electron micrographs of dispersions of ISPL used in in vitro and in vivo experiments in this application show specific morphological changes with the addition of a Mini-B construct. The simulated cow lung surfactant lipids without the construct consist of flat sheets with some vesicles of one to two microns in diameter (top of figure). In contrast simulated cow lung surfactant lipids with the Mini-B construct have many multi-vesicular liposomes that are similar to the morphology and size distribution of the microstructure observed in most commercial preparations containing native SP-B protein.

In the preceding paragraphs, specific embodiments are described. It will, however, be evident that various modifications and changes may be made thereto without departing from the broader spirit and scope of the claims. For example, a Mini-B construct was described formed by a synthetic route utilizing particular C-terminal and N-terminal peptide portions available at the Protein Data Bank. It is appreciated that in one instance certain amino acids of these peptides may be substituted for others with similar properties. It is also appreciated that amino acids may be added to either of these peptides without modifying the properties characteristic of an SP-B protein. The specification and drawings are, accordingly, to be regarded in an illustrative rather than a restrictive sense.

What is claimed is:

1. An exogenous peptide comprising SEQ ID NO: 3.
2. A composition comprising an exogenous peptide of claim 1, wherein the peptide further comprises a beta sheet.
3. A composition comprising an exogenous peptide of claim 1, and a lipid moiety.
4. A composition comprising an exogenous peptide of claim 1, and an additional treatment agent.
5. A kit comprising an exogenous peptide of SEQ ID NO: 3 and an additional treatment agent.
6. The kit of claim 5, wherein the treatment agent is selected from the group consisting of drugs, hormones, and vaccines.
7. The kit of claim 5, wherein the treatment agent comprises a biomolecule.
8. A kit of claim 5, wherein the peptide and the treatment agent are separately contained.

* * * * *

SEQUENCE LISTING

<160> NUMBER OF SEQ ID NOS: 3

<210> SEQ ID NO 1
<211> LENGTH: 25
<212> TYPE: PRT
<213> ORGANISM: Unknown
<220> FEATURE:
<223> OTHER INFORMATION: C-Terminal Segment of Surfactant Protein B

<400> SEQUENCE: 1

Phe Pro Ile Pro Leu Pro Tyr Cys Trp Leu Cys Arg Ala Leu Ile Lys
1               5                   10                  15

Arg Ile Gln Ala Met Ile Pro Lys Gly
            20                  25

<210> SEQ ID NO 2
<211> LENGTH: 16
<212> TYPE: PRT

-continued

```
<213> ORGANISM: Unknown
<220> FEATURE:
<223> OTHER INFORMATION: N-Terminal Segment of Surfactant Protein B

<400> SEQUENCE: 2

Gly Arg Met Leu Pro Gln Leu Val Cys Arg Leu Val Leu Arg Cys Ser
1               5                   10                  15

<210> SEQ ID NO 3
<211> LENGTH: 34
<212> TYPE: PRT
<213> ORGANISM: Unknown
<220> FEATURE:
<223> OTHER INFORMATION: Surfactant Protein B Mimic

<400> SEQUENCE: 3

Cys Trp Leu Cys Arg Ala Leu Ile Lys Arg Ile Gln Ala Met Ile Pro
1               5                   10                  15

Lys Gly Gly Arg Met Leu Pro Gln Leu Val Cys Arg Leu Val Leu Arg
            20                  25                  30

Cys Ser
```